United States Patent [19]

Springmann

[11] 4,288,389
[45] Sep. 8, 1981

[54] PROCESS FOR SEPARATING SULFONIC ACIDS FROM THE REACTION PRODUCTS OBTAINED WHEN PARAFINS ARE REACTED WITH SULFUR DIOXIDE, OXYGEN AND WATER IN THE PRESENCE OF ULTRA-VIOLET LIGHT

[75] Inventor: Hermann Springmann, Haltern, Fed. Rep. of Germany

[73] Assignee: Chemische Werke Hüls AG, Marl, Fed. Rep. of Germany

[21] Appl. No.: 211,623

[22] Filed: Dec. 1, 1980

[30] Foreign Application Priority Data

Feb. 8, 1980 [DE] Fed. Rep. of Germany ....... 3004651

[51] Int. Cl.³ ............................................. C07C 139/00
[52] U.S. Cl. ................................................. 260/504 S
[58] Field of Search ..................................... 260/504 S

[56] References Cited

U.S. PATENT DOCUMENTS

| 4,177,208 | 12/1979 | Boy et al. | 260/504 S |
| 4,178,307 | 12/1979 | Boy et al. | 260/504 S |

*Primary Examiner*—Alan Siegel
*Attorney, Agent, or Firm*—Gilbert L. Wells

[57] ABSTRACT

A process for separating sulfonic acids from the reaction product obtained by reacting paraffins with sulfuric acids, oxygen and water in the presence of ultra-violet light where an alcohol is used as an extractant.

The reaction product is treated with an aromatic alcohol as the extractant where the general formula of the alcohol is:

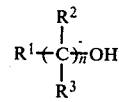

wherein:

$R^1$ is a phenyl group possibly substituted by halogen atoms and/or alkyl groups with 1 to 6 C atoms;
$R^2$ and $R^3$ denote hydrogen;
n is an integer from 1 to 3; and
$R^2$ may also be a methyl group when n=1.

Three phases are formed with the center phase as the alcohol phase. The alcohol phase is isolated from the remaining phases and the sulfonic acids are separated from this center alcohol phase.

4 Claims, No Drawings

PROCESS FOR SEPARATING SULFONIC ACIDS FROM THE REACTION PRODUCTS OBTAINED WHEN PARAFINS ARE REACTED WITH SULFUR DIOXIDE, OXYGEN AND WATER IN THE PRESENCE OF ULTRA-VIOLET LIGHT

CROSS REFERENCE TO RELATED APPLICATION

Applicant claims priority under 35 U.S.C. 119 for application P 30 04 651.6, filed Feb. 8, 1980 in the Patent Office of the Federal Republic of Germany

BACKGROUND OF THE INVENTION

The field of the invention is the after treatment of the sulfonation products of non-aromatic hydrocarbon mixtures and the state of the art may be ascertained by reference to West Germany Pat. No. 827,065 and U.S. Pat. No. 4,177,208, the disclosures of which are incorporated herein.

It is known that aliphatic and cycloaliphatic alcohols having at least 5 C atoms in the molecule can be used as extractants to extract the organic components from a crude sulfonation mixture containing unreacted paraffin, water and sulfuric acid besides the desired sulfonic acids, as disclosed in U.S. Pat. No. 4,177,208. In the process, the sulfuric acid separates in the aqueous phase and thus it can be isolated from the alcohol extract. The unreacted paraffin present together with the sulfonic acids remains in the lighter weight organic phase. The entire amount of paraffin present then is separated after neutralization of the sulfonic acids and removal of the extractant from the sulfonic acids present in the form of alkali sulfonates in a further process stage. This process of U.S. Pat. No. 4,177,208 includes the following steps:

(a) admixing with the paraffin sulfonic acid solution, at least one slightly polar alcohol selected from the group consisting of aliphatic and cycloaliphatic alcohols containing at least 5 carbon atoms, having a solubility in water less than 7% by weight which forms an azeotrope with water, thereby forming a mixture having an organic phase containing paraffin sulfonic acids dissolved therein and an aqueous phase containing the sulfuric acid;

(b) separating the organic phase from the aqueous phase;

(c) neutralizing the separated organic phase by admixture with a composition selected from the group consisting of alkali metal hydroxides, alkali metal carbonates, alkaline earth metal oxides, alkaline earth metal hydroxides, and alkaline earth metal carbonates thereby converting the sulfonic acids present in the organic phase into sulfonates, and forming a neutralized organic phase wherein the ratio of the amount of water to the amount of slightly polar alcohol in the neutralized phase is at most equal to the corresponding ratio for the azeotrope which forms between water and the slightly polar alcohol; and (d) removing the volatile components from the neutralized organic phase to recover the sulfonates under temperature and pressure conditions whereby the sulfonates are in a molten state.

It is furthermore known from West German Pat. No. 827,065 to purify and concentrate alkali sulfonates of high-molecular aliphatic hydrocarbons by extracting their aqueous solutions. Such solutions are obtained by treating the industrial saponification products of corresponding higher-molecular aliphatic hydrocarbon-sulfochlorides with a mineral acid, with higher alcohols or their mixtures only slightly soluble in water or not at all soluble and be treating thereupon the alcohol solution sequentially with water and alkali liquor.

Higher aliphatic or aromatic alcohols are suitable for the extraction, preferably such hydroaromatic alcohols as cyclohexanol and methylcyclohexanol. Contrary to what is the case for the process disclosed in U.S. Pat. No. 4,177,208, the process of the German Pat. No. 827,065 calls for removing the unreacted paraffin in a separate process stage prior to the treatment with the alcohol.

Thus, according to both processes of the prior art, the unreacted paraffin and the sulfuric acid obtained as a by-product (in the case of the sulfoxidation) or the chlorides (in the case of the sulfochlorination) are removed from the sulfonation mixture in two separate process stages.

SUMMARY OF THE INVENTION

It is therefore the object of the present invention to create a process allowing in one stage the removal of both the sulfuric acid and the unreacted paraffin extensively from the desired sulfonic acids of the reaction product obtained by reacting paraffins with sulfur dioxide, oxygen and water in the presence of ultra-violet light.

This object is surprisingly achieved according to the present invention wherein particular aromatic alcohols are substituted for the aliphatic and cycloaliphatic alcohol extractants of U.S. Pat. No. 4,177,208 and a three-phase system is formed with the uppermost layer consisting extensively of unreacted paraffins.

According to the present invention:

(a) paraffins are reacted with sulfur dioxide (sulfuric acid) oxygen and water in the presence of ultra-violet light to form a reaction product containing paraffin sulfonic acids, sulfuric acid, water and paraffins which have not reacted;

(b) the reaction product is treated with an aromatic alcohol as an extractant to form a three-phase system wherein the uppermost layer consists extensively of unreacted paraffins, the center layer contains the paraffin sulfonic acid and the lower layer is an aqueous solution of sulfuric acid;

(c) the center layer is separated from the other phases and the other phases are recycled to step (a);

(d) the paraffin sulfonic acids are separated from the aromatic alcohol of the center layer; and (e) the aromatic alcohol is recycled to step (a).

The aromatic alcohols used as the extractant of the present invention have the general formula:

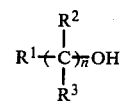

wherein:

$R^1$ is phenyl residue possibly substituted by halogen atoms and/or alkyl groups having 1 to 6 C atoms, preferably 1 to 3 C atoms;

$R^2$ and $R^3$ denote hydrogen;

n is an integer from 1 to 3, and $R^2$ may also be a methyl group if n is 1.

DESCRIPTION OF THE PREFERRED EMBODIMENTS

The process of the present invention starts first with the crude reaction product obtained when paraffins are reacted with sulfur dioxide, oxygen and water in the presence of ultra-violet light, sulfoxidation by the light-/water method as disclosed in CHEMIE IN UNSERER ZEIT, Vol. 13, (1979), pp. 157. Besides, obviously, sulfonation mixtures obtained from other methods may also be used provided they form a three-phase system with the alcohols suitable in the present invention. Alcohols of the general formula are for instance benzyl alcohol, alpha-phenylethanol, beta-phenylethanol, 3-phenylpropanol-(1) and p-methylbenzylalcohol and benzyl alcohol is preferred.

Usually the procedure followed in implementing the process of the present invention is such that the sulfoxidation product is reacted at a temperature between 10° and 60° C., preferably 20° to 40° C., with 20 to 100% by weight, preferably 40 to 60% by weight, especially preferred with about half the amount by weight (50% by weight) of the aromatic alcohol, and is mixed well. The mixing can take place in any commercial mixing unit, for instance an agitated vessel, and the optimum mixing time is easily ascertained by a few trials and errors. Following a short settlement time (about 1-2 minutes), three clear separation layers form, the upper one consisting extensively of paraffin, the center one containing the sulfonic acids dissolved in the extractant, and the lower layer containing the sulfuric acid generally as an aqueous solution of 15 to 25% by weight, preferably 18 to 21% by weight. The three layers are easily separated from one another. The separation can take place both continuously and discontinuously.

The recovery of the alcohol (center) phase may be implemented in various ways. In depends mostly whether the free sulfonic acids or the sulfonates, preferably alkali sulfonates, are desired.

To obtain the free sulfonic acids, the aromatic alcohol is removed for instance by azeotropic distillation as in U.S. Pat. No. 4,177,208 at a pressure at most equal to atmospheric. To that end the water in the alcohol solution of the sulfonic acids is so controlled that the total amount of the alcohol in the azeotropic mixture is distilled off with that water. The sulfonic acids are obtained in the bottom part of the distillation column in the form of a liquid which can be neutralized for any conversion into sulfonates.

The procedure for separating the sulfonic acids in the form of sulfonates is to treat the alcohol extract (center layer) with a basic compound before the alcohol is removed as in U.S. Pat. No. 4,177,208. Suitable basic compounds are hydroxides and carbonates of the alkali metals, preferably sodium and potassium hydroxides and carbonates, also oxides, hydroxides and carbonates of the earth alkali metals, preferably calcium oxide, hydroxide and carbonate. Sodium hydroxide as a basic compound and hence as a neutralizer is especially preferred.

The basic compounds furthermore can be used in solid form or as alcohol solutions or aqueous solutions and in proportions sufficient at least to neutralize the total quantity of the sulfonic acids. Preferably the proportion of basic compound used slightly exceeds the stoichiometric amounts, for instance up to 1.2 valent weight of the basic compound per valent weight of sulfonic acid.

The sulfonic acidic salts then are freed in the alcohol solution so treated, for instance by a thin-film evaporator as in U.S. Pat. No. 4,177,208, from the extractant, the paraffin still present and not separated, and the water. The sulfonates are removed as fusion products from the sump of the evaporator. A mixture of the aromatic alcohol used as extractant, of the residual paraffin and water is obtained as the head product and separates when forming into three phases into the components alcohol, paraffin and water which, following suitable reprocessing, as was the unreacted paraffin from the first separation operation, is recycled into the process.

The process of the present invention applies especially to treating crude sulfonated paraffin solutions produced by sulfoxidizing n-paraffins where the molecules comprise 7 to 30, preferably 10 to 20 C atoms.

The products obtained or isolated by the present process, free paraffin sulfonic acids or their alkali or earth alkali salts, are predominantly used for formulating detergents.

The examples below illustrate the process of the present invention.

All data, unless otherwise indicated, are in % by weight.

EXAMPLE 1

6,000 g of a sulfoxidation product composed as follows:

| | |
|---|---|
| paraffin oil ($C_{14}$–$C_{17}$) | 35.6% by weight |
| monosulfonic acid | 20.9% by weight |
| disulfonic acid | 2.7% by weight |
| sulfuric acid | 7.2% by weight |
| water | 33.6% by weight | are reacted with 3,000 g of benzyl alcohol and thoroughly mixed at room temperature. After standing for a short while (1–2 minutes), three clear phases form, which can easily be separated from one another. The upper phase (1,728 g) contains the paraffin mixture and about 1% of benzyl alcohol, the center phase (5,518 g) contains the sulfonic acids extract in benzyl alcohol, and the lower phase (1,725 g) contains an aqueous 22.4% sulfuric acid.

A degree of separation of 90.8% results for the sulfuric acid and of 80.1% for the paraffin, each referred to the sulfuric acid and paraffin oil initially present in the mixture.

Thereupon, the separated center phase is adjusted with a 50% by weight aqueous sodium hydroxide solution to a pH of 11-12. Next the sodium salts of the sulfonic acids are freed by vaccum distillation (10 mbar) from the solvent, the residual amounts of paraffin and the water. The clear residue so obtained is easily pulverized. The residue composition is the following:

| | |
|---|---|
| monosulfonate | 83.8% by weight |
| di- and polysulfonate | 7.9% by weight |
| paraffin | 0.4% by weight |
| sodium sulfate | 4.5% by weight |
| sodium hydroxide | 0.3% by weight. |

EXAMPLE 2

400 g of sulfoxidation product (reactor discharge) of the following composition:

| | |
|---|---|
| paraffin ($C_{14}$–$C_{17}$) | 33.9% by weight |
| monosulfonic acid | 20.4% by weight |
| disulfonic acid | 2.8% by weight |
| sulfuric acid | 7.7% by weight |
| water | 34.7% by weight | are mixed with 200 g of beta-phenylethanol. In a short time three easily separable phases are formed:

| | |
|---|---|
| upper phase | (104.7 g) |
| center phase | (386 g) |
| lower phase | (126.1 g). |

The lower phase contains 22.2% by weight of sulfuric acid. This corresponds to a calculated degree of separation of 91% for the sulfuric acid. The upper phase contains about 1% by weight of benzyl alcohol, resulting in a degree of separation of 76.4% for the paraffin referred to the paraffin quantity in the reactor discharge. The center phase is separated and processed as in Example 1.

EXAMPLE 3

The same starting material as in Example 2 is reacted with alpha-phenylethanol (0.5 parts by weight per 1 part by weight of reactor discharge). The three phases so obtained are separated. There is a 55% separation for the paraffin, 96% for the sulfuric acid, each referred to the initial amount present. The separated center phase is processed as in Example 1.

EXAMPLE 4

1 Part by weight of the same starting material as in Example 2 is reacted with 0.5 parts by weight of 3-phenylpropanol-(1), mixed, and the three layers so obtained are separated. In the lower phase, 93.7% of the initially present sulfuric acid are separated, and in the upper phase, 62.6% of the paraffin. The separated center phase is processed as in Example 1.

I claim:

1. A process for separating the sulfonic acids in an untreated paraffin sulfonic solution containing in addition to said paraffin sulfonic acids, sulfuric acid, water and non-sulfonated paraffins, which comprises:
   (a) admixing with the paraffin sulfonic acid solution, at least one aromatic alcohol having the general formula

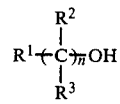

wherein:
   $R^1$ is a phenyl group, said phenyl group possibly substituted by halogen and/or alkyl groups having 1 to 6 C atoms;
   $R^2$ and $R^3$ are hydrogen;
   n is an integer from 1 to 3; and
   $R^2$ is a methyl group when n=1, thereby forming a mixture having three phases wherein the uppermost layer consists essentially of unreacted paraffins, the center layer consists essentially of paraffin sulfonic acids and the lower layer consists essentially of an aqueous solution of sulfuric acid;
   (b) separating said center layer; and
   (c) said aromatic alcohol is separated from said center layer to produce said sulfonic acids.

2. The process of claim 1, wherein said aromatic alcohol of the general formula is selected from the group consisting of benzyl alcohol, alpha-phenylethanol, beta-phenylethanol, 3-phenylpropanol-1 and p-methylbenzyl alcohol.

3. The process of claim 2, wherein said aromatic alcohol is benzyl alcohol.

4. The process of claim 2, wherein about 20 to 100% by weight of said aromatic alcohol is mixed with said paraffin sulfonic acid solution.

* * * * *